United States Patent [19]

Kato

[11] Patent Number: 4,488,808
[45] Date of Patent: Dec. 18, 1984

[54] PRINT INSPECTING DEVICE

[75] Inventor: Yasuo Kato, Tokyo, Japan

[73] Assignee: Dai Nippon Insatsu Kabushiki Kaisha, Tokyo, Japan

[21] Appl. No.: 548,025

[22] Filed: Nov. 2, 1983

Related U.S. Application Data

[63] Continuation of Ser. No. 221,802, Dec. 31, 1980, abandoned.

[30] Foreign Application Priority Data

Jan. 9, 1980 [JP] Japan ................................. 55-1051

[51] Int. Cl.³ .......................................... G01N 21/88
[52] U.S. Cl. ..................................... 356/73; 250/556; 356/402; 356/425; 364/551

[58] Field of Search .................. 356/71, 72, 237, 402, 356/403, 406, 407, 425, 394, 448, 73, 430; 250/555, 556, 562, 563; 364/526, 550-552

[56] References Cited

U.S. PATENT DOCUMENTS 3,588,513 6/1971 Akamatsu .......................... 356/430
4,197,584 4/1980 Blazek ................................. 364/551

Primary Examiner—F. L. Evans
Attorney, Agent, or Firm—Koda and Androlia

[57] ABSTRACT

In a print inspecting device, the entire print area is scanned by a plurality of light emitting and receiving units arranged in one straight line to obtain image data from the print, and the image data thus obtained are compared with the standard data also obtained by scanning a standard print, to determine the print acceptability.

8 Claims, 10 Drawing Figures

FIG. I
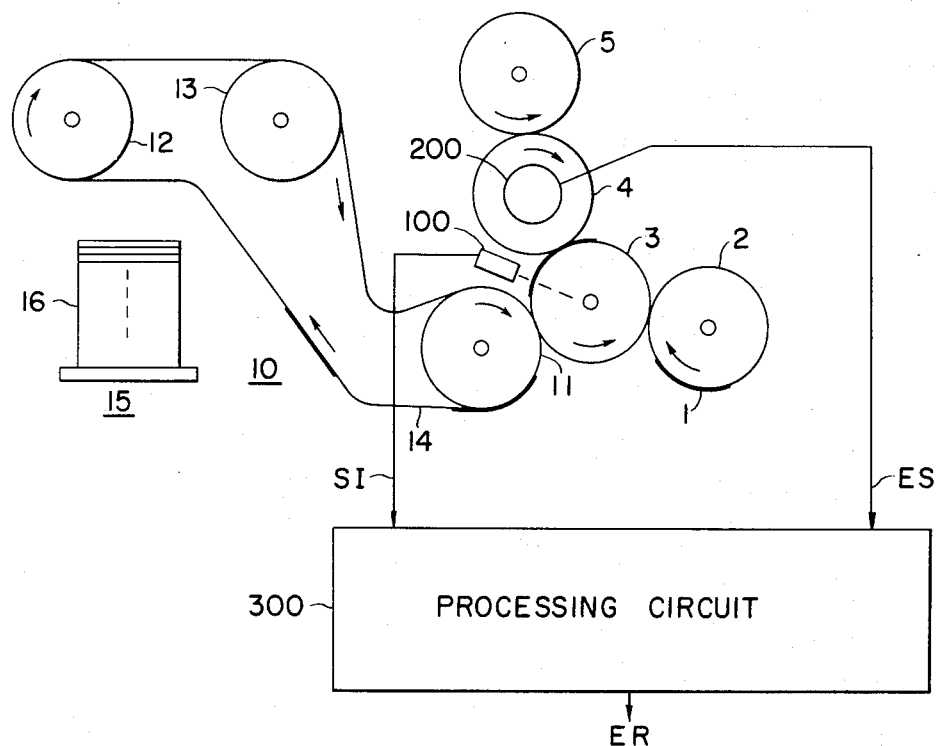
FIG. 2
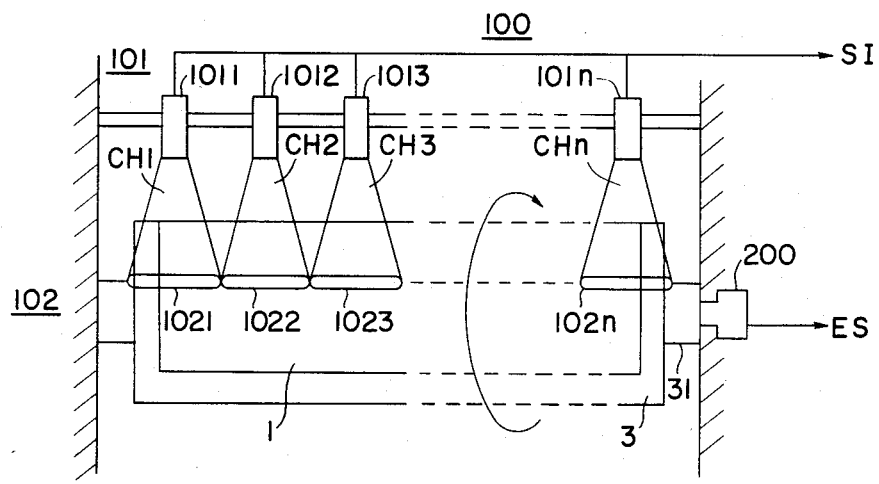

FIG. 10

PRINT INSPECTING DEVICE

This is a continuation of application Ser. No. 221,802 filed Dec. 31, 1980, now abandoned.

BACKGROUND OF THE INVENTION

This invention relates to a device for inspecting the quality of prints in a sheet-feed press, a rotary press and a rewinder.

A variety of print inspecting devices have been proposed in the art. In one of these conventional devices, tone marks or color patches printed in the marginal portions of prints have been inspected to determine the acceptability of the prints. But in the conventional device, the defective portions (such as for instance partially unsatisfactory tones) disappearing in the tone marks or color patches could not be detected, and it is necessary to provide the marginal portions for prints, in which the marks or patches should be printed.

Furthermore, the devices in which data have been obtained from a printed pattern have been also known in the art. In one of the devices, one sensor is used to input the data of the entire area of a pattern printed. In another device, the print area is scanned with a minute spot. But the former device could not detect a large area print with high accuracy, although it was effective in inspecting a small area print such as a brochure. The latter device has taken a lot of time to achieve the data input so that it could not inspect a large area print at high rate.

Furthermore, a comparison system in which a reference data is compared with the next surface data to determine the print acceptability, and a comparison system in which a reference data is compared with the previous inspection data, are known in the art.

However, the former system could not inspect an only-one-image, that is, it cannot be applied to all kinds of prints, and therefore the adjustment was troublesome when the group of print is changed. The latter system could detect positively the defective portions (such as stains due to dripped oil) appearing suddenly in prints, but it could not detect moderate tone change lasting for a long time.

SUMMARY OF THE INVENTION

In view of the foregoing, an object of this invention is to provide a print inspecting device in which all of the above-described difficulties accompanying a conventional print inspecting device or system have been eliminated.

BRIEF DESCRIPTION OF THE DRAWINGS

In the accompanying drawings:

FIG. 1 is an explanatory diagram outlining a printing machine to which the technical concept of this invention is applicable;

FIG. 2 is also an explanatory diagram showing the arrangement of an optical detecting device employed in the invention;

FIG. 10 is a diagram for a description of the relation between divided input regions and an integration operation.

DETAILED DESCRIPTION OF THE INVENTION

Figure 3:
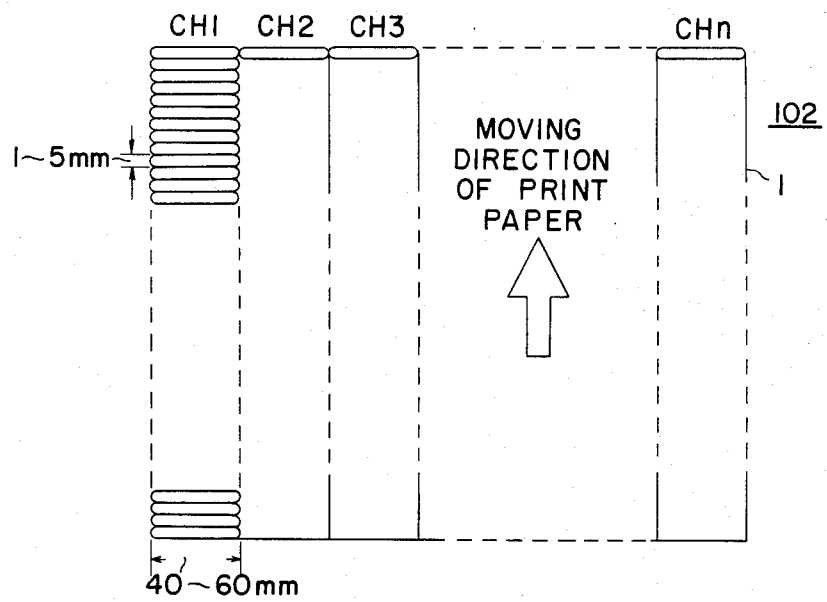
FIG. 3 is a diagram for a description of the relation between the scanning of a print and the light beam spots of a detecting head.

FIG. 1 shows a final printing unit and a sheet taking-off section in a sheet printing machine or a sheet-feed press to which the technical concept of this invention is applicable. As shown in FIG. 1, a sheet 1 passes between a delivery cylinder 2 and an impression cylinder 3 and then between the impression cylinder 3 and a blanket cylinder 4 which is operated in association with a plate cylinder 5, so that the sheet 1 is printed. The sheet 1 thus printed is delivered to a taking-off cylinder 11, and is then loaded, by means of loading pawls (not shown), on a conveying chain 14 which is laid over the taking-off cylinder 11 and sprockets 12 and 13. The sheet (or print) 1 thus loaded is conveyed towards the sprocket 12. When the sheet 1 reaches a delivery position 15, the loading pawls are released to drop the sheet 1, as a result of which the sheet 1 is stacked as a delivered sheet 16. According to the invention, a multi-channel system optical detecting device 100 for inputting image data from the surface of the print 1 which is placed on the rotating impression cylinder 3 is provided, and a rotary encoder 200 is also provided so that it operates in association with the blanket cylinder 4. Furthermore, a processing circuit 300 is provided according to the invention, which operates to process a detection signal SI outputted by the optical detecting device 100 and an encoder signal ES outputted by the rotary encoder 200, and to output an error signal ER when a printed sheet is detected unsatisfactory as a result of the decision which is made to determine whether or not the print is satisfactory in quality.

The optical detecting device 100, as shown in FIG. 2, comprises a plurality of light emitting and receiving unit 1011, 1012, 1013, ... and 101n (generally designated by reference numeral 101) forming n channels (or a multi-channel system). These units 1011 through 101n are arranged in one straight line along the axis of the impression cylinder 3. The illumination regions 1021, 1022, 1023, ... and 102n of the light emitting and receiving units 1011 through 101n are circular; however, they appear as elongated light spots about 1 to 5 mm in width in the direction of movement of the print and about 40 to 60 mm in length when detected. That is, the illumination regions 1021 through 102n are arranged as if they were an axially extended straight line formed with the elongated light spot, so that the data of the entire surface of the print 1 can be inputted in division manner (i.e. the entire surface can be scanned with the light spots). The size of the light spot can be determined as desired according to the size of a print and the contents of an image.

The rotary encoder 200 is mounted on the rotary shaft 31 of the impression cylinder 3 through a gear mechanism so that the rotary encoder 200 is rotated at a predetermined speed.

FIG. 3 shows the positional relationships between the illumination regions 102 of the light emitting and receiving units 101 and the print 1 spread flat. As is apparent from FIG. 3, the image data of the entire surface of the print 1 are optically inputted in division manner as the print 1 is moved. More specifically, the image data are inputted by intermittently carrying out the input operations of the light emitting and receiving units 1011 through 101n in synchronization with the conveyance of the print 1. Accordingly, a print area corresponding to one revolution of the plate is optically divided into a number of smaller areas each being equal to the area of the elongated light spot. Thus, each light spot provides the data of one picture element.

Figure 4:
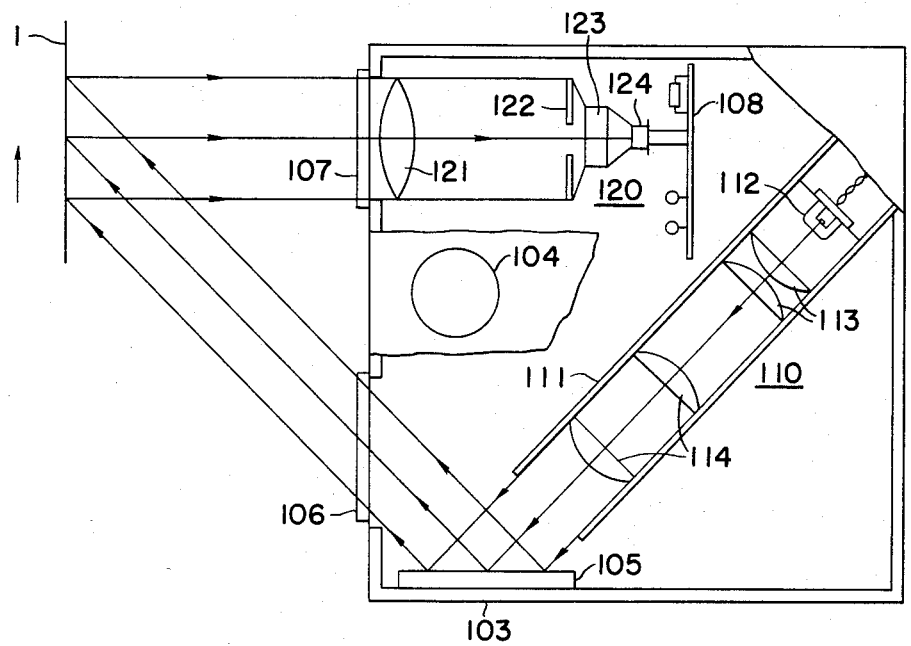
FIG. 4 is an explanatory diagram showing the arrangement of one example of a light emitting and receiving unit in the optical detecting device.

The arrangement of each of the light emitting and receiving units 101 forming the optical detecting device 100 is as shown in FIG. 4. A light emitting unit 110 for emitting light and a light receiving unit 120 for receiving light from the print 1 to convert the light into electrical data are provided in a housing 103. The housings 103 of the light emitting and receiving units 101 are connected together by inserting a mounting bar into holes 104 formed in the housings 103, thus forming the above-described optical detecting device 100 covering all the channels 1 through n.

The light emitting unit 110 has a cylindrical pipe 111 open at one end. A lamp 112 (such as a halogen lamp or a tungsten lamp) is provided as a light source in the pipe 111 at the other end. A pair of condenser lenses 113 are disposed in front of the light source 112 in the pipe 111, and a pair of projection lenses 114 is provided at the light emission output section of the pipe 111. Light from the light emitting unit 110, after being reflected by a reflection mirror 105 on the bottom of the housing 103, is applied through a light emitting slit 106 to the print 1 on the impression cylinder 3 which is being rotated, in such a manner that the light forms a predetermined angle with the print 1. Light from the print 1 is applied through a light receiving slit 107 to the light receiving unit 120. The light receiving unit 120, as shown in FIG. 4, comprises: a condenser lens 121 for condensing incident light; a slit 122 for intercepting the light condensed by the condenser lens 121 into one rectangular in section; a cylinder lens 123 for condensing the light from the slit 122 into a spot light or a circular light; and a photoelectric converter 124 consisting of a pair of light receiving elements for providing an electrical signal in response to the quantity of light from the cylinder lens 123. The photoelectric converter 124 may be the color sensor (manufactured by Sharp Co., In Japan) which is one chip made up of two photodiodes different in sensitivity, or two sensors different in sensitivity which are arranged on the light condensing plane.

Figure 5:
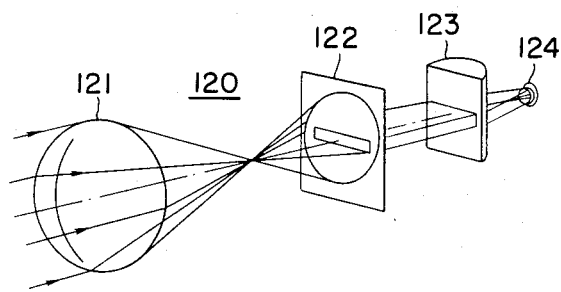
FIG. 5 is an explanatory diagram showing the path of light in a light receiving unit in the light emitting and receiving unit shown in FIG. 4.
Figure 6:
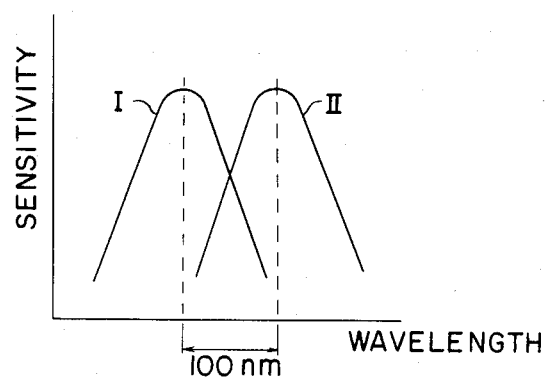
FIG. 6 is a graphical representation indicating the characteristic curves of a two-element type photoelectric converter employed in the invention.

In the light receiving unit 120, the light advances as illustrated in FIG. 5. The output signal of the photoelectric converter 124 is applied to an amplifier 108, where it is amplified and outputted as a detection signal SI. The photo-electric converter 124 is made up of two light receiving elements (such as silicon photo-diodes) as described above. The sensitivity characteristics of the two light receiving elements are different by about 100 nm in peak value, with respect to optical wavelength, as indicated by I and II in FIG. 6, so that the spectral characteristics of the print can be obtained.

Now, the arrangement of the processing circuit 300 which processes the detection signal SI outputted by the optical detecting device 100 and the encoder signal ES provided by the rotary encoder 200, will be described.

Figure 7:
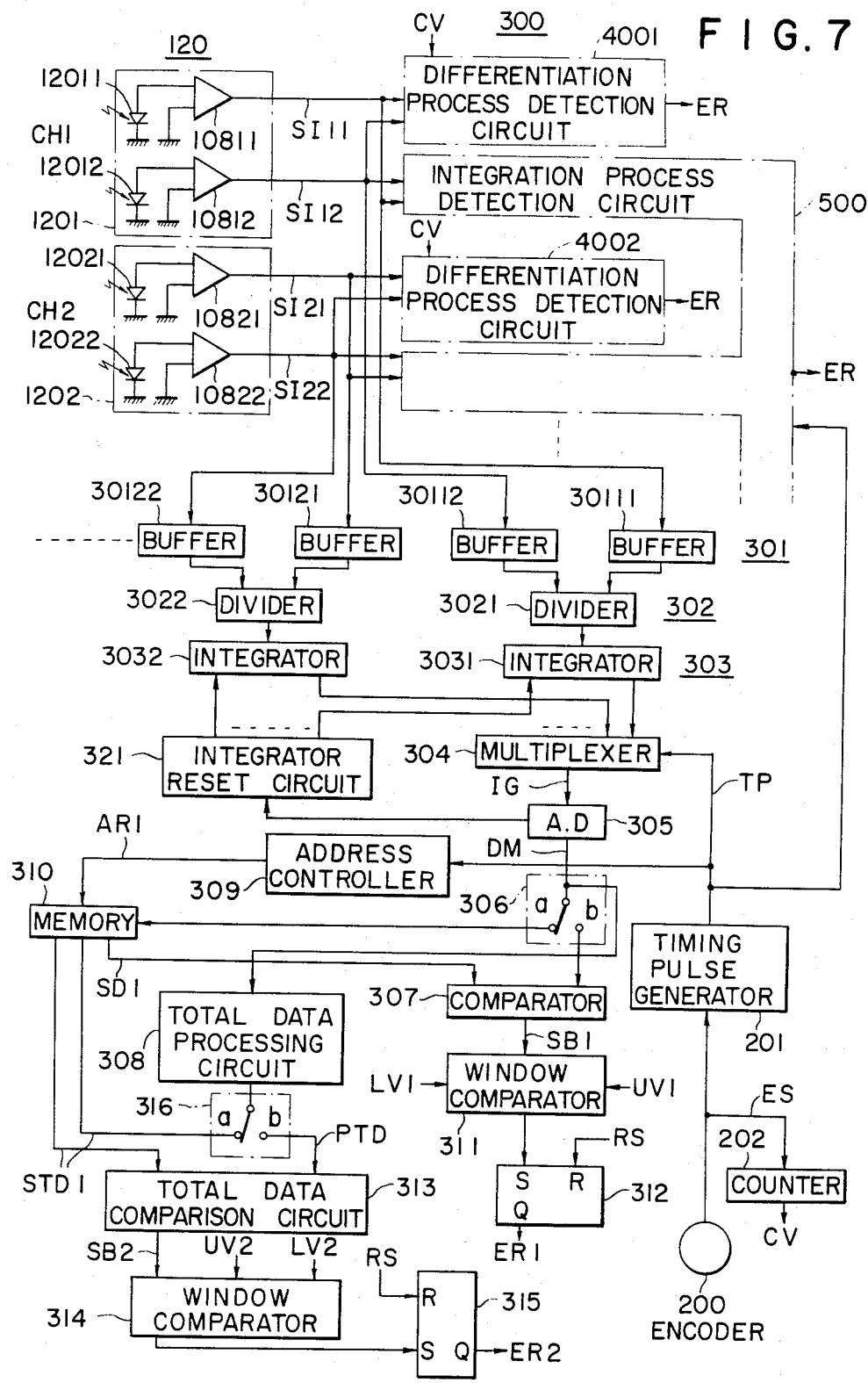
FIG. 7 is a block diagram showing one example of a processing circuit according to the invention.

FIG. 7 shows one example of the arrangement of the processing circuit 300. However, it should be noted that, for the sake of clarity and simplification in description, the light receiving units 120 and the relevant circuits illustrated in FIG. 7 are only for two channels CH1 and CH2.

In the light receiving unit 1201 of the channel CH1, the output of a first light receiving element 12011 is provided through an amplifier 10811 as a detection signal SI11, which is applied to a differentiation process detection circuit 4001(400) and an integration process detection circuit 500, and to a divider 3021 in the channel CH1 through a buffer circuit 30111. On the other hand, the detection signal SI12 which is outputted through an amplifier 10812 by a second light receiving element 12012 is applied to the differentiation process detection circuit 4001(400) and the integration process detection circuit 500, and to the divider 3021 of the channel CH1 through a buffer circuit 30112. The output detection signal SI21 of a first light receiving element 12021 in the light receiving unit 120 of the channel CH2 is similarly applied to a differentiation process detection circuit 4002 and the integration process detection circuit 500, and to a divider 3022 through a buffer circuit 30121. The output detection signal SI22 of a second light receiving element 12022 is also applied to the differentiation process detection circuit 4002 and the integration process detection circuit 500, and to the divider 3002 through a buffer circuit 30122. The above-described operation is similarly carried out for the remaining light receiving units 120 of the channels CH3, CH4, . . . and CHn. The division outputs of the dividers 3021, 3022, . . . 302n, after being integrated by integrators 3031, 3032, . . . 303n respectively, are applied to a multiplexer 304. The division outputs thus applied are selectively outputted by the multiplexer 304 with the aid of a timing pulse TP provided by a timing pulse generating circuit 201 which processes the rotary encoder signal ES. The output of the multiplexer 304 is applied as an integration signal IG to an analog-to-digital (A-D) converter 305, which it is converted into a digital data DM. The digital data DM is applied through a switch circuit (such as a data selector) 306 to a comparison circuit 307 and a total data processing circuit 308. The A-D conversion completion in the A-D converter 305 is detected from the strobe signal or the like of the A-D converter 305 by an integrator resetting circuit 321, whereby the integrators 303 are reset and a memory 310 applies the relevant standard data SD1 to the comparison circuit 307. In the comparison circuit 307, the difference data SB1 between the detection (or inspection) data DM of this time and the relevant standard data SD1 which has been stored in advance is obtained. The difference data SB1 is supplied to a window comparator 314. In the window comparator 314, the upper limit value UV1 and the lower limit value LV1 for determining threshold values have been preset. When the difference data SB1 exceeds the threshold values, the window comparator 314 sets a flip-flop circuit 313, so that the latter 313 outputs an error signal ER1.

On the other hand, after all the picture elements have been inspected, an address controller 309 controls the memory 310 so that a standard total data STD1 is applied to a total data comparison circuit 313. In the comparison circuit 313, the difference data SB2 between the standard total data STD1 and the total data of this time which is provided by the total data processing circuit 308 is obtained, and it is then subjected to decision in a window comparator 314. When the difference data SB2 exceeds the preset threshold values UV2 and LV2, the window comparator sets a flip-flop circuit 315, so that the latter 315 outputs an error signal ER2. The above-described total data processing and comparison are accomplished before the next print to be inspected reaches the detecting device. The flip-flop circuits 312 and 315 are reset by reset signals which are provided separately.

All the differentiation process detection circuits 4001, 4002, . . . 400n are identical in arrangement. One example of the arrangement of the differentiation process detection circuit will be described with reference to FIG. 8.

For instance, the detection signal SI11, through the amplifier 10811, of the first light receiving unit 12011 of the channel CH1 is applied to a differentiation circuit 401, which it is subjected to differentiation, as a result of which a differentiation signal DS is outputted by the differentiation circuit 401. The differentiation signal DS is applied to three comparators 402, 403 and 404, which have threshold setting units 405, 406 and 407, respectively. The outputs of the comparators 402, 403 and 404 are applied to monostable multivibrators 408, 409 and 410, where they are subjected to waveform shaping, respectively. The output differentiation data signals DF1, DF2 and DF3 of the multivibrators 408, 409 and 410 are applied to gate circuits 411, 412 and 413, respectively, and to an address controller 414. The outputs of the gate circuits 411 through 413 are supplied to the set terminals of flip-flop circuits 415, 416 and 417, and error signals ER3, ER4 and ER5 are provided at the set output terminals Q of the flip-flop circuits 415, 416 and 417, respectively.

On the other hand, the encoder signal ES from the rotary encoder 200 is counted by a counter 202. The count value CV of the counter 202, which is representative of a position data, is applied through a switch circuit 420 to a memory 421, where it is stored according to an address signal AR2 from the address controller 414. The memory 421 supplies memory position data MP1, MP2 and MP3 corresponding to the set level systems of the aforementioned comparators 402, 403 and 404 to comparison circuits 422, 423 and 424. When the data MP1, MP2 and MP3 coincide with the count value CV of the counter 202 which is supplied through the switch circuit 420, the comparison circuits 402, 403 and 404 output coincidence signals CD1, CD2 and CD3, respectively. These coincidence signals CD1, CD2 and CD3 are subjected to waveform shaping in monostable multivibrators 425, 426 and 427 and are then applied to the gate circuits 411, 412 and 413, respectively. When all the picture elements have been inspected, the memory 421 supplies a standard total data PTD2 to a total data comparison circuit 430, which it is compared with the total data of this time. When the difference between the two data exceeds the predetermined upper and lower limit values UV10 and LV10, it is determined that the print is unsatisfactory, and a flip-flop circuit 432 outputs an error signal ER6.

The set values of the setting units 405, 406 and 407 are different from one another. It is assumed that the setting units 405, 406 and 407 set 1 V, 2 V and 3 V. Then, if the differentiation signal DS is 2.5 V, the differentiation data signals DF1 and DF2 are outputted. If the differentiation signal DS is 3.5 V, then the differentiation data signals DF1, DF2 and DF3 are outputted. If the signal DS is 0.5 V, then none of the differentiation data signals DF1 through DF3 are outputted.

The flip-flop circuits 415 through 417 and 432 are reset by reset signals which are provided separately.

Figure 9:
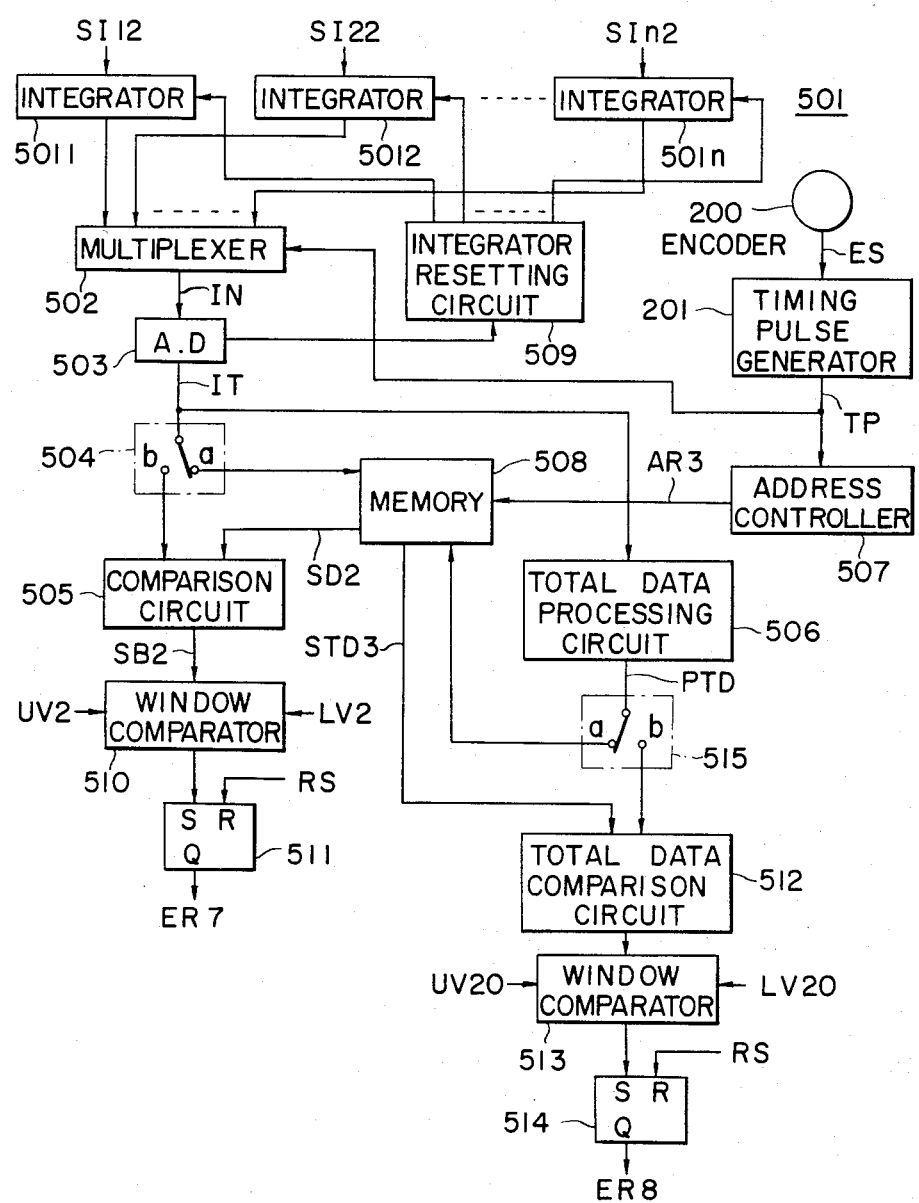
FIG. 9 is a block diagram showing the arrangement of one example of an integration process detection circuit in the invention.

One example of the arrangement of the integration process detection circuit 500 will be described with reference to FIG. 9. The detection signals SI12 through SIn2 from the channels CH1 through CHn are integrated in integrators 5011, 5012, . . . and 501n (501), respectively, and are applied to a multiplexer 502. The detection signals thus applied are selectively outputted by the multiplexer 502 with the aid of the timing pulse TP provided by the timing pulse generating circuit 201. Thus, the output of the multiplexer 502 is applied as an integration signal IN to an A–D (analog-to-digital) converter 503, where it is converted into a digital integration data signal IT. The integration data signal IT is applied to a comparison circuit 505 through a switch circuit 504, and to a total data processing circuit 506. The standard data SD2 which is stored in a memory 508 is supplied to the comparison circuit 505, where it is compared with the integration data signal IT. The difference data SB2 between the standard data SD2 and the integration data signal IT is applied to a window comparator 510. When the difference data SB2 exceeds the upper limit value UV2 and the lower limit value LV2, a flip-flop circuit 511 is set, and its set output is provided as an error signal ER7.

On the other hand, when all the picture elements have been inspected, the memory 508 outputs a standard total data STD3, which is compared with the total data of this time which is provided by the total data processing circuit 506, in the comparison circuit 505. When the difference between the two total data exceeds the predetermined reference values UV20 and LV20, it is determined that the print is unsatisfactory, and a flip-flop circuit 514 outputs an error signal ER8. Similarly as in the above-described cases, the flip-flop circuits 511 and 514 are reset by the reset signal RS which is provided separately.

When the inspection of the print is started, the lamps 112 in the optical detecting device 100 are turned on, and the counters, flip-flop circuits, etc. in the processing circuit 300 are reset. Then, the levels of the setting units 405 through 407 in the differentiation process detection circuits 4001, 4002, . . . are set to suitable values, and the armatures of the switch circuits 306, 316, 420, 433, 504 and 515 are tripped to their contacts a by the operator, respectively, to obtain the standard data.

When all the preparatory operations have been achieved as described above, first the operation of obtaining the standard (reference) data is carried out. More specifically, the print 1 which is used for detecting and storing the standard data is delivered to the final printing unit shown in FIG. 1. The print 1 reaches the detection section of the optical detecting device 100, after passing between the roller 2 and the impression cylinder 3 and between the impression cylinder 3 and the blanket cylinder 4. In this detection section, as shown in FIGS. 2 and 3 the spot light 102 is projected in the form of an axially extended straight line. Accordingly, as the impression cylinder 3 is rotated, the image data of the entire area of the print 1 are inputted in division manner by the light emitting and receiving units 1011 through 101n; that is, the image data of each picture element is inputted. In this operation, as shown in FIG. 4, the parallel rays from the light emitting unit 110 in each light emitting and receiving unit 101, after being reflected by the plane mirror 105, is applied through the light emitting slit 106 to the print 1. The light reflected from the print 1 is applied through the slit 107 and the light receiving unit 120 to the photo-electric converter 124. The photoelectric converter 124 is made up of one pair of light receiving elements different in spectral sensitivity characteristic, as described before. For instance, in the case of the channel CH1, as was described before with reference to FIGS. 7 through 9, the detection signal SI11 of the light receiving element 12011 is applied to the differentiation process detection circuit 4001 and the integration process detection circuit 500, and to the buffer circuit 30111, while the detection signal SI12 of the light receiving element 12012 is applied to the differentiation process detection circuit 4001 and the integration process detection circuit 500, and to the buffer circuit 30112. Since the light receiving elements 12011 and 12012 in the photoelectric converter 124 are different in sensitivity characteristic, and the values of the output detection signals SI11 and SI12 are also different. The degree of the difference between the values is obtained by the divider 3021. The output of the divider 3021 is integrated by the integrator 301 and is then applied to the multiplexer 304. The same operation is carried out for the remaining channels CH2 through CHn. The output integration values of the integrators 303 in all the channels are applied to the multiplexer 304. On all the integration values, one is selected and outputted by the multiplexer 304 with the aid of the timing pulse TP provided by the timing pulse generating circuit 201. This selecting operation will be described with reference to FIG. 10.

Figure 10:
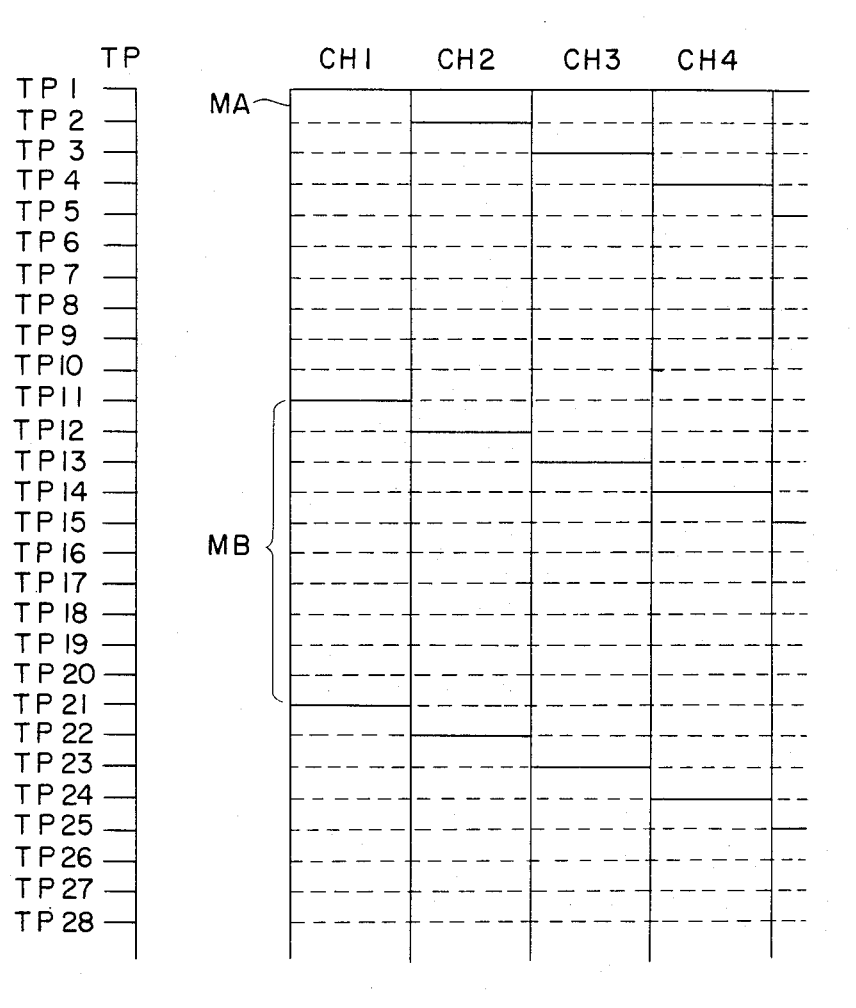

In FIG. 10, reference character MA designates a picture element indicating a region of the print 1, which correspond to a unitary division region in each channel provided by the spot light 102, and reference character MB designates an integration region consisting of ten (10) picture elements MA. In FIG. 10, the number of picture elements MA forming one integration region is ten (10); however, it may be determined suitably according to the size of a print and the contents of an image.

The timing pulse generating circuit 201 generates the timing pulse TP (TP1, TP2, TP3 and so forth) whenever the boundary of the picture element MA occurs. In response to the timing pulses TP1, TP2, ... thus outputted, the multiplexer 304 is switched successively to select the integration signals IG of the integrators 3031, 3032, 3033, ... (303), and the integration signals IG thus selected are applied to the A-D converter 305 successively, where they are converted into the digital integration signals. The digital integration signals are applied through the contact a of the switch circuit 306 to the memory 310, where they are stored. At the same time, the A-D converter strobe signals for resetting the integrators are applied to the integrator resetting circuit 321. The memory 310 is so designed as to store the signals according to the address signals AR1 from the address controller 309 which is controlled by the timing pulse TP. The integrator resetting circuit 321 resets the relevant integrators 303 upon detection of the completion of the analog-to-digital conversion. For instance, when an integrator 303 has integrated the data of ten picture elements, the integrator resetting circuit 321 resets the integrator 303. Thus, the integrations values for the standard data have been stored in the memory 310, and are outputted, as the standard data SD1, to the comparison circuit 307 later during the inspection period. In the total data processing circuit 308, the total data such as for instance correlation data are obtained. The total data are applied through the contact a of the switch circuit 316 to the memory 310, where the total data are stored as the standard total data, and are applied, as the standard total data STD1, to the total data comparison circuit 313 later during the inspection period.

Figure 8:
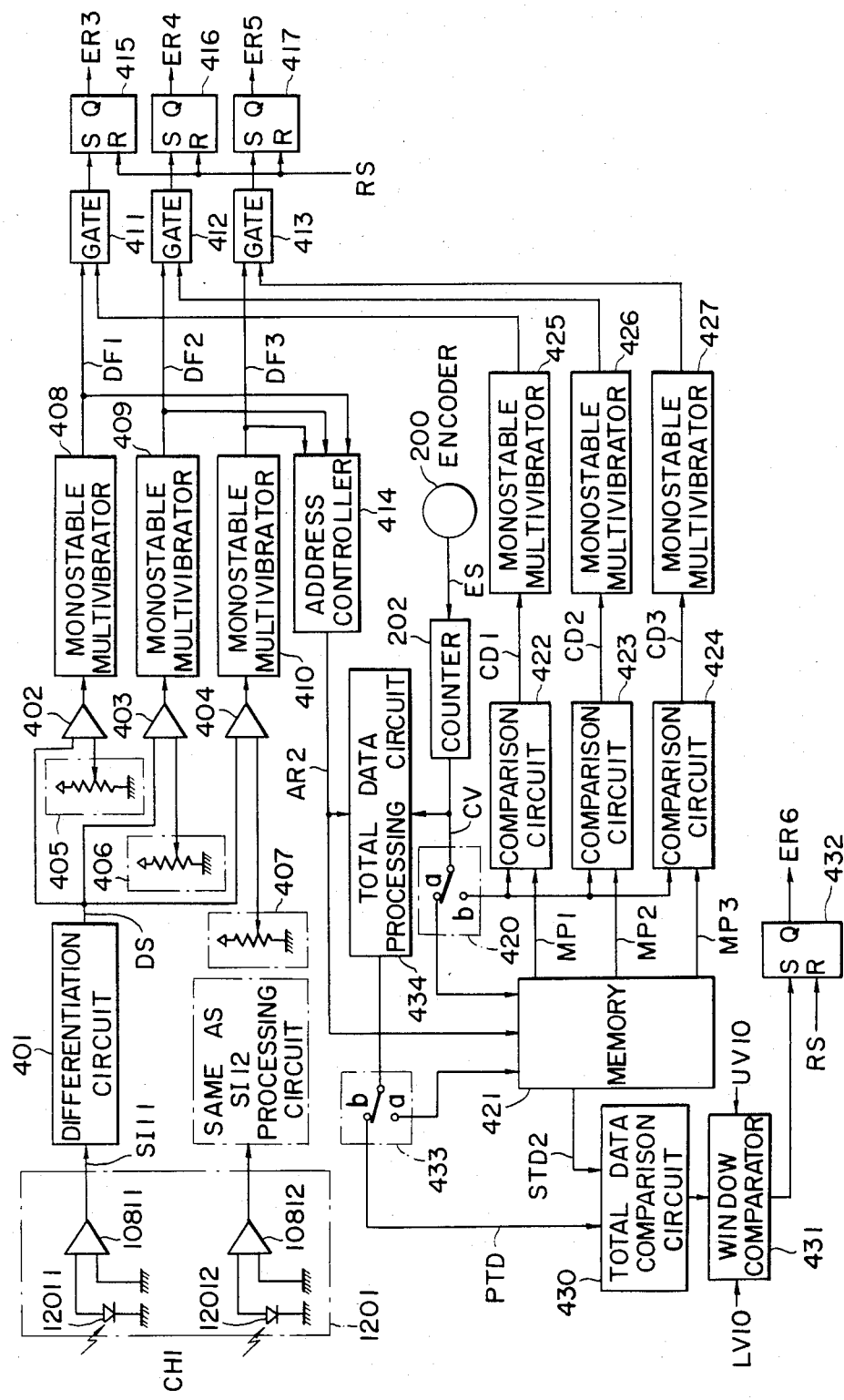
FIG. 8 is a block diagram showing the arrangement of one example of a differentiation process detection circuit in the invention.

The standard data storing operation of the differentiation detection circuit 400 will be described with reference to FIG. 8.

The output detection signal SI11 of the light receiving element 12011 in the light receiving unit 1201 (120) is supplied to the differentiation circuit 401, the differentiation signal DS of which is applied to the first input terminals of the comparators 402, 403 and 404. The different set values of the setting units 405, 406 and 407 are applied to the second input terminals of the comparators. When the differentiation signal DS exceeds the thresholds of the set values, the comparators 402 through 404 outputs the pulse signals, which are applied to the monostable multivibrators 408, 409 and 410, respectively. The pulse signals thus applied are subjected to waveform shaping in the monostable vibrators, and are outputted as the differentiation data signals DF1, DF2 and DF3, respectively. These signals DF1, DF2 and DF3 are applied to the gate circuits 411, 412 and 413, and to the address controller 414. As a result, the address controller 414 outputs the address signal AR2. In response to the address signal AR2, the count value CV of the counter 202 is applied through the contact a of the switch circuit 420 to the memory 421, where it is stored. Thus, the position data (the count value CV) for the standard data have been stored in the memory, and are outputted as the memory position data MP1 through MP3 to the comparison circuits 422 through 424 later during the inspection period. On the other hand, the total data such as for instance correlation data are obtained from the position data (CV) of the differentiation outputs in the total data processing circuit 434. The total data thus obtained are applied through the contact a of the switch circuit 433 to the memory 421, where the data are stored as the standard total data. The standard total data thus stored are applied, as the standard total data STD2, to the total data comparison circuit 430 later during the inspection period.

The standard data storing operation in the integration process detection circuit 500 will be described with reference to FIG. 9.

The output detection signals SI12 through SIn2 of the light receiving units 120 of the channels are supplied to the integrators 5011 through 501n, and the integration signals are applied to the multiplexer 502. The outputs of the multiplexer 502 are successively selected with the aid of the timing pulses TP (TP1, TP2, ... ), and the selected output, or the integration signal IN is inputted to the A-D converter 503, where it is converted into the digital integration signal IT representative of the density characteristic. The integration signal IT is applied to the memory 508 through the contact a of the switch circuit 504 so that it is stored in the memory 508, while the A-D converter strobe signal for resetting the relevant integrator is applied to the integrator resetting circuit 509. The storing of the integration signal in the memory 508 is carried out according to the address signal AR3 from the address controller 507 which is controlled by the timing pulse TP. Upon detection of the completion of the A-D conversion, the integrator resetting circuit 509 resets the relevant integrator 501. When the integrator 501 has integrated, for instance, the data of ten picture elements, the integrator outputs its contents and is then resetted. Thus, the integration values for the standard data have been stored in the memory 508, and are outputted, as the standard data SD2, to the comparison circuit 505.

In the total data processing circuit 506, the total data such as correlation data are obtained from the data of the integrator. The total data thus obtained are applied through the contact a of the switch circuit 515 to the memory 508, where the data are stored as the standard total data and is applied, as the standard total data STD3, to the total data comparison circuit 512 later during the inspection period.

The data of the standard (reference) print 1 are inputted in division manner, and the processed data thereof are successively stored in the memory 310 (spectral characteristic), the memory 421 (differentiation characteristic) and the memory 5058 (integration characteristic), and when the data of all the picture elements have been processed, the standard total data are stored in the memories 310, 421 and 508, whereupon the armatures of the switch circuits 306, 316, 420, 433, 504 and 515 are tripped from the contact a over to the contact b automatically or by the operator.

Similarly as in the standard (reference) print, the data of the print to be inspected are optically inputted in division manner. In this operation, the strobe signal of the A-D converter 305 is applied to the integrator resetting circuit 321 to carry out the resetting operation similarly as in the above-described case, and the output data DM is applied to the comparison circuit 307 through the contact b of the switch circuit 306, and to the total data processing circuit 308. The difference data SB1 between the data DM of this time supplied by the A-D converter 305 and the standard data SD1 which has been obtained and is supplied by the memory 310 is obtained successively in the comparison circuit 307, and it is applied to the window comparator 311. When the difference data SB1 is between the upper limit value UV1 and the lower limit value LV1, no operating signal is outputted by the window comparator 311. When the difference data SB1 exceeds the upper limit value UV1 or the lower limit value LV1, i.e. when the present inspection data is detected abnormal, the window comparator 311 outputs the operating signal to set the flip-flop circuit 312, so that the latter 312 outputs the error signal ER1. Upon provision of the error signal ER1, the printing machine is stopped, or an alarm device such as an alarm buzzer or lamp is operated.

In the total data processing circuit 308, the total data such as correlation data are obtained with respect to the present inspection data. The total data thus obtained are compared with the standard total data STD1 in the total data comparison circuit 313. When the present inspection data are detected abnormal by the window comparator 314, the error signal ER2 is outputted by the flip-flop circuit 315.

In a print, a picture element is in close relation to the surrounding picture elements, and the patterns (such as tones) are distributed in a probability sense. Therefore, if the statistical data of the distribution are obtained in advance, then it can be determined according to the statistical data whether or not the print is satisfactory. For instance, if the similarity of a picture element to the surrounding picture elements is obtained and one print surface is divided into some classes according to a so-called "similarity ratio determination method", then the decision can be carried out with the values inherent to the classes and the number of classes as decision data.

Furthermore, whether the print is satisfactory or not can be determined by the following method: The dispersion data, standard difference data and power spectra (obtained by subjecting the self-correlation function to Fourier transformation) of a picture element and the surrounding picture elements thereof in a standard print are obtained through mathematical process with the flow of picture element data as a time function. The data of a print to be inspected are obtained in the same way. Both data thus obtained are compared, to determine whether the print is satisfactory or not. The above-described processing and decision are carried out in the total data processing circuit 308, the total data comparison circuit 313 and the window comparator 314, as a result of which, when the print is determined unsatisfactory, then the flip-flop circuit 315 outputs the error signal ER2.

In the differentiation process detection circuit 400 also, the count value CV of the counter 202 is applied through the contact b of the switch circuit 420 to the comparison circuits 422, 423 and 424, in which the count value is compared with the memory position data MP1, MP2 and MP3 which have been obtained in advance. When the count value coincides with the data MP1, MP2 and MP3, the comparison circuits 422 through 424 outputs the coincidence signals CD1 through CD3, respectively. The coincidence signals CD1 through CD3 are applied to the monostable multivibrators 425 through 427, where they are subjected to waveform shaping and are then applied to the gate circuits 411 through 413, respectively. The present differentiation data signals DF1 through DF3 have been applied to the gate circuits 411 through 413, respectively. Accordingly, it is determined whether or not the coincidence signals CD1 through CD3 coincide with the present differentiation data signals DF1 through DF3. When the coincidences are not obtained, it is determined that the print is locally unsatisfactory, and the gate circuits 411 through 413 outputs the signals to set the flip-flop circuits 415 through 417, so that the error signals ER3 through ER5 are outputted by the flip-flop circuits 415 through 417, respectively. Similarly as in the above-described case, the total data PTD of the present inspection is obtained in the total data processing circuit 430. The total data PTD is compared with the standard total data STD2 in the total data comparison circuit. When the print is detected unsatisfactory by the window comparator 431, the flip-flop circuit 432 outputs the error signal ER6. Thus, the defects or unsatisfactory tones over the entire print can be detected.

In the integration process detection circuit 500, the integration signal IT outputted by the A-D converter 503 is applied to the integrator resetting circuit 509, to carry out the resetting operations similarly as in the above-described case, and the integration signal IT is applied through the contact b of the switch circuit 504 to the comparison circuit 505 and the total data processing circuit 506. The difference data SB2 between the present data IT from the A–D converter 503 and the standard data SD2 from the memory 508 is successively obtained in the comparison circuit 505, and is then applied to the window comparator 510. When the difference data SB2 is between the upper limit value UV2 and the lower limit value LV2 set in the window comparator 510, no operating signal is outputted by the latter 510. When the difference data SB2 exceeds the upper limit value UV2 or the lower limit value LV2, i.e. when the present inspection data is determined unsatisfactory, the operating signal is outputted by the window comparator 510 to set the flip-flop circuit 511, as a result of which the error signal ER7 is outputted by the latter 511. On the other hand, similarly as in the above-described case, the decision is carried out by the total data processing circuit 506, the total data comparison circuit 512 and the window comparator 513. When the print is determined unsatisfactory, the flip-flop circuit 514 outputs the error signal ER8.

As is clear from the above description, when the print is determined unsatisfactory by the print inspecting device according to the invention, the error signals ER1 through ER8 are outputted. Accordingly, by using the error signals, it can be carried out to operate a lamp or a buzzer to inform the occurrence of an unsatisfactory print or to stop the operations of the printing machine and the rewinding machine. Furthermore, in the case of a sheet-feed press of sheet delivery type or a rotary press of sheet delivery type, the satisfactory prints can be separated from the unsatisfactory prints so that the satisfactory and unsatisfactory prints are delivered to different positions, or only the unsatisfactory prints can be automatically removed. In the case of a web rotary press, it is impossible to remove only the unsatisfactory print portions. However, in this case, a sheet or tape can be inserted into the portion of the web where the print is unsatisfactory, or the portion can be sprayed or coated with a magnetic or heat-sensitive paint or punched, or the edge of the portion can be cut, so that after the web has been printed, the printing corresponding to the portion is conducted again.

As is apparent from the above description, in the print inspecting device, the entire area of the pattern on a print is inspected. Accordingly, it is unnecessary to provide special tone marks or color patches, and therefore it is unnecessary to provide margins for such tone marks or color patches. No matter what portion of a print is unsatisfactory, the unsatisfactory print can be positively detected. Furthermore, the input head assembly is in the multichannel arrangement according to the invention, and the input region of each head is so shaped that it is large in the widthwise direction and small in the print movement direction. Therefore, a large area print moving at high speed can be inspected accurately in real time mode. Especially, the picture elements are longer in the widthwise direction in the invention, and therefore the number of multi-channel input heads can be reduced, the fluctuations in characteristic of the detecting heads can be adjusted with ease, and the maintenance can be achieved readily. Since the picture elements are shorter in the print movement direction, the differentiation process detection efficiency can be improved, thus increasing the accuracy in detecting defects in a print which are considerably small in size like spots.

In addition, in the print inspecting device according to the invention, the density level and spectral characteristic data are obtained from a print to be inspected and are utilized in combination in the signal processing operation, and therefore the unsatisfactory-print detecting performance can be improved without making the device intricate. For instance, the drawback accompanying the conventional print inspecting device that, where a print has a portion unsatisfactory in hue, the defect cannot be detected because it is at the same density level, can be eliminated according to the invention. Moreover, as the differentiation process and the integration process are employed in combination in the signal processing operation, a very small defective portion in a print or a defect covering a larger area or the entire area of a print can be detected with high accuracy. Thus, all the defects in a print which attribute to printing, such as for instance the absence of color (in a part or the whole of a print), non-uniform color, tone shift, stains due to ink or oil and resister (front gauge and side gauge) can be detected according to the invention. As the decision as to whether or not the print is satisfactory is carried out by using the standard data, even the tone which changes gradually can be detected when the change exceeds the predetermined reference value, and a very small defective portion of the print can be positively detected.

With the device of the invention, the quality of prints which is heretofore inspected visually can be inspected automatically, which contributes to the labor saving. In addition, according to the invention, the print inspection range can be increased to the prints which could not be inspected because of the shortage of workers.

Since the picture element position data detected in the differentiation process are employed as the reference data in the decision of the acceptability of prints, the amount of information to be stored in the memories can be small, which results in a reduction of the number of memories and a compact circuit arrangement in the device of the invention.

Furthermore, in the invention, the process of converting analog data to digital data is unnecessary; that is, it is unnecessary to use A–D converters which heretofore make the signal processing speed low. Accordingly, high response speed (real time process) is obtained in the invention.

In subjecting the integration data of the blocks to analog-to-digital conversion, the analog-to-digital conversion timing is shifted for every block, i.e. (different conversion timing is employed for different blocks), and therefore only one A–D converter can be used commonly for the analog-to-digital conversions of the integration data of the different blocks, which contributes to the provision of a compact circuit arrangement. This is economically advantageous.

As a plurality of integrators are employed, all the area of a print can be inspected, and accordingly no matter what portion of a print is defective, the defect can be positively detected.

In the above-described embodiment of the invention, three threshold setting units are provided in the differentiation detection circuit; however, it is obvious that the number of threshold setting units can be changed as the case may be. Furthermore, in the above-described embodiment, the light emitting and receiving unit is so designed that it is one unit and it receives light reflected from a print; however, it may be so modified that it is divided into a light emitting section and a light receiving section and it receives light passed through a print.

What is claimed is:

1. A print inspecting device in which the surface of a print moving in one direction is optically scanned by light emitting and receiving means on a detecting head to obtain image data from a picture pattern on said print surface and said image data thus obtained is utilized to inspect whether or not said print is satisfactory, which comprises:

light emitting and receiving means forming a plurality of channels in which elongated light spots having a length perpendicular to the direction of movement of said print which is longer than a width thereof which is in the direction of movement of said print are provided adjacent to each other in a straight line such that a longitudinal direction of each light spot coincides with the direction of width of said print.

2. A device as claimed in claim 1, in which a light receiving means in each of said light emitting and receiving means comprises a slit and a cylinder lens by which a photoelectric conversion section receives light in a point or circular in section.

3. A device as claimed in claim 1, which comprises a spectral characteristic means for processing according to spectral characteristics a plurality of detection signals outputted by said light receiving means.

4. A device as claimed in claim 1, which comprises a circuit for differentiating and integrating outputs of said light receiving means, to detect local defects on the surface of said print and a defect spread over the entire surface of said print.

5. A device as claimed in claim 1, which comprises:
differential processing means for processing through differential image data from the entire print area;
memory means for storing standard-print differential process data provided by said differential process means; and
comparison means for comparing the present data provided by said differential process means with said standard print differential process data stored in said memory means, an output of said comparison means being utilized to determine whether or not said print is satisfactory.

6. A device as claimed by claim 5, in which said standard print differential process data is position data as to said print.

7. A device as claimed in claim 1 which comprises:
integral processing means for processing through integral image data from the entire print area for every block consisting of a predetermined number of picture elements;
memory means for storing standard-print integral processing data provided by said integral process means; and
comparison means for comparing the present data provided by said integral processing means with said standard data stored in said memory means,
an output of said comparison means being utilized to determine whether or not said print is satisfactory.

8. A device as claimed in claim 7, in which said integral process means comprises:
a plurality of integral processing means;
a multiplexer for successively switching outputs of said integral processing means; and
an analog-to-digital converter for converting an output of said multiplexer into a digital signal.

* * * * *